(12) United States Patent
Kraus et al.

(10) Patent No.: US 8,546,257 B2
(45) Date of Patent: Oct. 1, 2013

(54) ELECTRODE ARRAYS AND METHODS OF FABRICATING THE SAME USING PRINTING PLATES TO ARRANGE PARTICLES IN AN ARRAY

(75) Inventors: Tobias Kraus, Saarbruecken (DE); Laurent Malaquin, Linas (FR); Heiko Wolf, Pfaeffikon (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/551,159

(22) Filed: Jul. 17, 2012

(65) Prior Publication Data

US 2012/0282771 A1    Nov. 8, 2012

Related U.S. Application Data

(62) Division of application No. 12/117,000, filed on May 8, 2008, now abandoned.

(51) Int. Cl.
*H01L 21/28* (2006.01)
(52) U.S. Cl.
USPC ............... 438/674; 257/780; 257/E21.171
(58) Field of Classification Search
USPC ........................................................ 438/674
See application file for complete search history.

(56) References Cited

U.S. PATENT DOCUMENTS

| | | | |
|---|---|---|---|
| 5,586,892 A | 12/1996 | Sato | |
| 5,616,206 A | 4/1997 | Sakatsu et al. | |
| 5,891,366 A | 4/1999 | Gruenwald et al. | |
| 5,965,064 A | 10/1999 | Yamada et al. | |
| 6,555,408 B1 | 4/2003 | Jacobsen et al. | |
| 6,623,579 B1 | 9/2003 | Smith et al. | |
| 6,683,663 B1 | 1/2004 | Hadley et al. | |
| 7,191,930 B2 * | 3/2007 | Bednarz et al. | 228/245 |
| 8,028,621 B2 | 10/2011 | Kraus et al. | |
| 2004/0229032 A1 | 11/2004 | Cobbley et al. | |
| 2005/0082655 A1 | 4/2005 | Nishi et al. | |
| 2005/0110406 A1 | 5/2005 | Jeong et al. | |
| 2005/0146053 A1 | 7/2005 | Lee | |

(Continued)

FOREIGN PATENT DOCUMENTS

| WO | 2005015792 A2 | 2/2005 |
|---|---|---|
| WO | 2006052104 A1 | 5/2006 |

OTHER PUBLICATIONS

Tobias Kraus, Laurent Malaquin, Emmanuel Delamarche, Heinz Schmid, Nichols D. Spencer, and Heiko Wolf, "Closing the Gap Between Self-Assembly and Microsystems Using Self-Assembly, Transfer and Integration of Particles," Advanced Materials, 2005, pp. 2438-2442, Wiley-VCH Verlag GmbH & Co. KGaA, Weinheim.

(Continued)

*Primary Examiner* — Calvin Lee
*Assistant Examiner* — Abul Kalam
(74) *Attorney, Agent, or Firm* — Cantor Colburn LLP; Daniel Morris

(57) ABSTRACT

Electrode arrays and methods of fabricating the same using a printing plate to arrange conductive particles in alignment with an array of electrodes are provided. In one embodiment, a semiconductor device comprises: a semiconductor topography comprising an array of electrodes disposed upon a semiconductor substrate; a dielectric layer residing upon the semiconductor topography; and at least one conductive particle disposed in or on the dielectric layer in alignment with at least one of the array of electrodes.

10 Claims, 2 Drawing Sheets

(56) References Cited

U.S. PATENT DOCUMENTS

| | | |
|---|---|---|
| 2005/0150684 A1 | 7/2005 | Hashimoto |
| 2005/0191448 A1 | 9/2005 | Suh et al. |
| 2005/0227475 A1 | 10/2005 | Chen et al. |
| 2006/0003097 A1 | 1/2006 | Andres et al. |
| 2007/0001313 A1 | 1/2007 | Fujimoto et al. |
| 2007/0023908 A1 | 2/2007 | Fork et al. |
| 2007/0138460 A1 | 6/2007 | Choi et al. |
| 2007/0155184 A1 | 7/2007 | Yi et al. |
| 2007/0187840 A1 | 8/2007 | Dell'Acqua-Bellavitis et al. |
| 2009/0047485 A1 | 2/2009 | Ofir et al. |
| 2009/0278213 A1 | 11/2009 | Kraus et al. |
| 2011/0244192 A1 | 10/2011 | Kraus et al. |

OTHER PUBLICATIONS

Tobias Kraus, Laurent Malaquin, Heinz Schmid, Walter Riess, Nicholas D. Spencer and Heiko Wolf, "Nanoparticle Printing with Single-Particle Resolution," Sep. 7, 2007, vol. 2, Nature Publishing Group, pp. 1-7.

Min Jung Lee et al., "Polyelectrolyte Micropatterning Using Agarose Plane Stamp and a Substrate Having Microscale Features on Its Surface," Bull. Korean Chem. Soc., vol. 26, No. 10, 2005; pp. 1-4.

U.S. Appl. No: 13/159,662; Final Office Action; Date Filed: Jun. 14, 2011; Date Mailed: Mar. 18, 2013; pp. 1-13.

* cited by examiner

ELECTRODE ARRAYS AND METHODS OF FABRICATING THE SAME USING PRINTING PLATES TO ARRANGE PARTICLES IN AN ARRAY

CROSS-REFERENCE TO RELATED APPLICATION

This application is a divisional of U.S. patent application Ser. No. 12/117,000, filed May 8, 2008, the disclosure of which is incorporated by reference herein in its entirety.

FIELD OF THE INVENTION

This invention relates to semiconductor device fabrication, and particularly to electrode arrays and methods of fabricating such arrays using a printing plate to arrange conductive particles in alignment with an array of electrodes.

BACKGROUND OF THE INVENTION

Substantial attention has been directed to the design, implementation, and use of array-based electronic systems for carrying out and/or monitoring biological systems. For example, electronic biosensors of various types have been used to monitor the progress of certain biological systems. Biosensors have been described that include an array of electrode test sites in electrical connection with a plurality of conductive leads. The electrode test sites can be formed in a semiconductor wafer using photolithography and etch processing techniques. Further, the test sites can be coupled to associated detection circuitry via transistor switches using row and column addressing techniques employed, for example, in addressing dynamic random access memory (DRAM) or active matrix liquid crystal display (AMLCD) devices.

There are ongoing efforts to increase the density of electrode arrays by reducing electrode and overlying lead or contact sizes to nanometer- or micrometer-scale dimensions, thereby producing "microelectrode arrays" (MEAs). However, it has been difficult to produce MEAs with very small dimensions using current top-down semiconductor fabrication methods. For example, current photolithography and etch techniques can be employed to pattern openings or vias in an insulation layer formed above the electrodes before filling those vias with a conductive material to form contacts to the electrodes. However, the ability of the photolithography and etch techniques to pattern small features is restricted by factors such as the resolution limits of the optical lithography system. It would therefore be desirable to develop a method for producing a large number of electrode arrays of relatively small dimensions at a relatively low cost.

SUMMARY OF THE INVENTION

The shortcomings of the prior art are overcome and additional advantages are provided through the provision of electrode arrays and methods of fabricating the same using a printing plate to arrange conductive particles in alignment with an array of electrodes. In one embodiment, a semiconductor device comprises: a semiconductor topography comprising an array of electrodes disposed upon a semiconductor substrate; a dielectric layer residing upon the semiconductor topography; and at least one conductive particle disposed in or on the dielectric layer in alignment with at least one of the array of electrodes.

In another embodiment, a method of fabricating a semiconductor device comprises: contacting a face of a printing plate with a suspension comprising conductive particles to arrange the particles at predefined positions on the face of the printing plate; and contacting a dielectric layer residing upon an array of electrodes disposed upon a semiconductor substrate with the face of the printing plate to transfer the conductive particles to a position in or on the dielectric layer.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Figure 1:
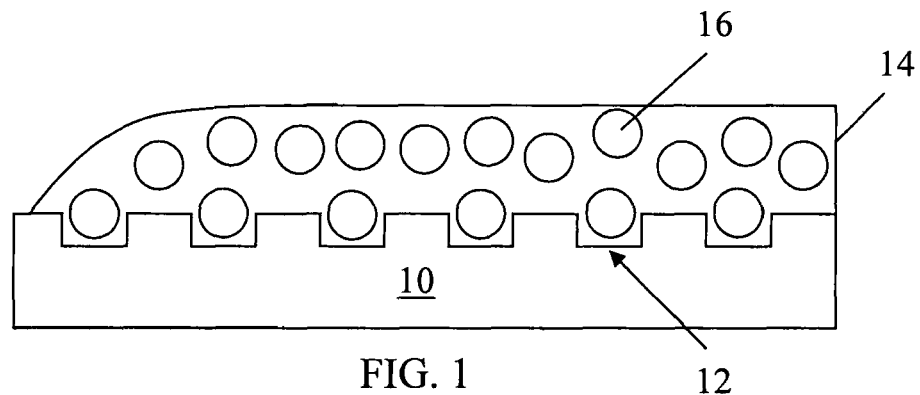
FIGS. 1-3 illustrate one example of a semiconductor fabrication method in which a printing plate is used to arrange conductive particles in alignment with an array of electrodes formed upon a semiconductor substrate and coated by a dielectric layer.
Figure 2:
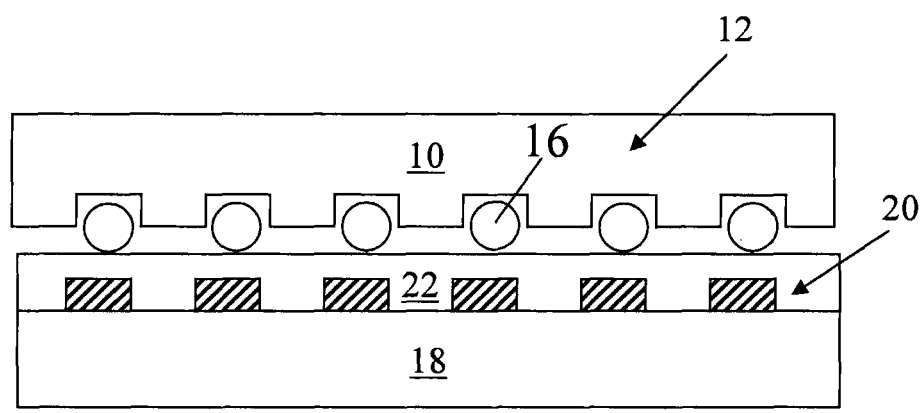
Figure 3:
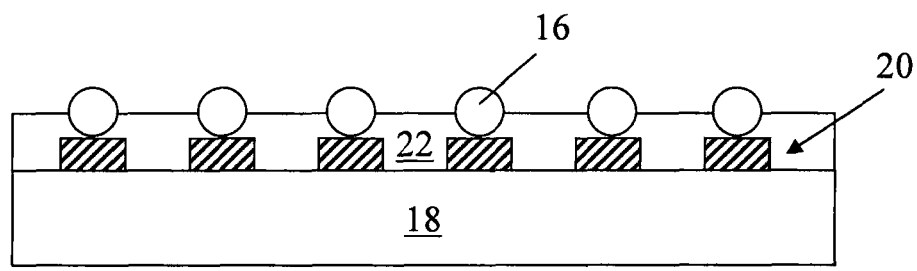

Turning now to the drawings in greater detail, it will be seen that FIGS. 1-3 illustrate an exemplary embodiment of a method for fabricating an array of electrodes comprising conductive particles printed in alignment with an array of flat electrodes formed above a semiconductor substrate using, for example, a directed assembly method. This method can be used to economically form an array of densely packed electrodes across a large area in a relatively short period of time. The electrode arrays described herein can be interfaced with biological systems.

As shown in FIG. 1, an array of electrodes can be fabricated by obtaining a printing plate 10 that includes an array of recessed features 12 on the face of the printing plate 10. The printing plate 10 can include a molded material that can replicate a three-dimensional relief structure by a molding process. Examples of suitable molded materials include but are not limited to as silicone, elastomers that can replicate a three-dimensional relief structure by a molding process (e.g. fluorinated polyethers), or combinations comprising at least one of the foregoing. The recessed features 12 of the printing plate 10 can be pre-selected to correspond with an array of flat electrodes formed upon a semiconductor substrate (discussed later). A suspension 14 comprising conductive particles 16 dispersed therein can be placed in contact with the face of the printing plate 10. As the suspension 14 is moved over the printing plate 10, e.g., on a movable stage, a particle 16 becomes embedded in each recessed feature 12 of the printing plate 10, as depicted in FIG. 1. In this manner, the conductive particles 16 are purposely arranged in the array of recessed features 12. When the particles 16 have assumed their desired positions, the liquid can be removed to form a dry, filled printing plate 10 that can be stored until it is desirable to transfer the particles 16 to a substrate. In another embodiment, the particles can be captured in protruding structures on the printing plate such as corners having 90° angles. In yet another embodiment, the particles can be captured on binding sites on the printing plate having chemical functionalities that specifically attract and bind the particles. Examples of such chemical functionalities include but are not limited to polyelectrolytes.

The particle suspension 14 shown in FIG. 1 can be formed by mixing the conductive particles 16 with a liquid. Examples of suitable liquids include but are not limited to ink, water, aqueous solutions comprising surfactants, alcohols (e.g., methanol, ethanol, propanol, and 2-propanol), and combinations comprising at least one of the foregoing (e.g., a water/alcohol mixture). The amount of particles present in the liquid can be about 0.01 to about 40% by weight, specifically about 0.01 to about 20% by weight, more specifically about 0.05 to about 10% by weight, and even more specifically about 0.1 to about 5% by weight. Examples of materials that can be present in the conductive particles 16 include but are not limited to metals (e.g., Cu, Au, Ag, Pt, Ir, W, Ta, Pd, Al, Ni, and Co), conductive oxides such as indium tin oxide (ITO), and combinations comprising at least one of the foregoing metals. In one embodiment, the particles 16 have a grain size dimension of less than or equal to about 100 micrometers (microns), more specifically less than or equal to about 100 nanometers (particles of this size are referred to as "nanoparticles"), to allow for the formation of densely packed electrode arrays. The term "grain size dimension" is herein defined as any straight lined segment that passes through the center of the particle and has its end points positioned at the surface of the particle. Although the particles 16 are depicted as being substantially spherical shaped, they can have other geometries such as cube shaped. Particles of such small dimensions can be synthesized by the reduction of the salts of the metals to be formed into particles.

Turning to FIG. 2, the particles 16 disposed in the recessed features 12 of the printing plate 10 can be transferred to a semiconductor topography comprising an array of flat electrodes 20 disposed upon a semiconductor substrate 18 and a dielectric layer 22 extending across the electrodes 20. The substrate 18 can comprise, for example, single crystalline silicon. The flat electrodes 20 can be formed into an array or matrix upon the substrate 18 by depositing a conductive material, e.g., a transition metal, across the substrate 18 and patterning the conductive material using photolithography followed by an etch technique such as a dry, plasma etch. In one embodiment, each electrode 20 has lateral dimensions (e.g., the width and the depth) of less than or equal to about 1000 micrometers, more specifically less than or equal to about 100 nanometers, such that a microelectrode array is formed. The dielectric layer 22 can be formed through the deposition of a thin dielectric material, e.g., a spin-deposited polymer, followed by the planarization of the surface of the dielectric material using, e.g., chemical mechanical polishing (CMP). The resulting dielectric layer 22 can have a substantially planar surface. Examples of suitable polymers for use in the dielectric layer 22 include but are not limited to polymethylmethacrylate (PMMA), polystyrene (PS), polyimide, polyurethanes (PU), spin-on glass, and combinations comprising at least one of the foregoing.

The transfer of the conductive particles 16 can be accomplished by positioning the printing plate 10 upside down on top of the dielectric layer 22 such that the particles 16 are aligned to the underlying electrodes 20. As a result of this positioning, the particles are "stamped" into the dielectric layer 22 to which they adhere due to their large surface interface. As shown in FIG. 3, after the removal of the printing plate 10, the conductive particles 16 remain in or on the dielectric layer 22 in their pre-selected positions, i.e., in alignment with the underlying array of electrodes 20. In this manner, a conductive particle 16 is positioned above each electrode 20. In an alternative embodiment, multiple particles could be printed on each electrode 20. Subsequently, the substrate 18 and the dielectric layer 22 can be heated above the glass transition temperature, $T_g$, of the dielectric material.

Figure 4:
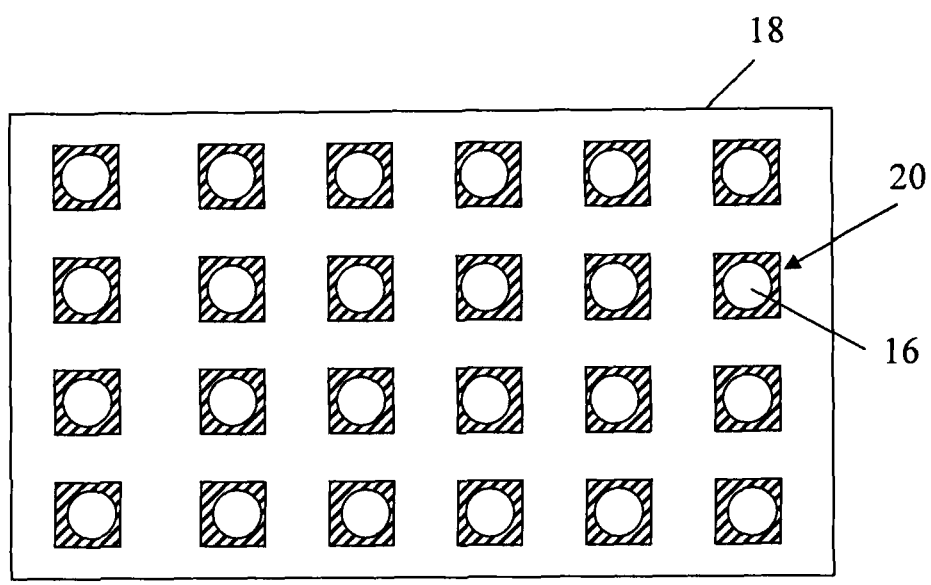
FIG. 4 illustrates one example of a semiconductor device comprising conductive particles arranged in alignment with an underlying array of electrodes.

The resulting alignment of the conductive particles 16 with the array of electrodes 20 is better illustrated in FIG. 4. In one embodiment, the electrodes 20 can be spaced apart by equivalent distances, thus forming an equidistantly spaced array. As a result of the printing step, the particles 16 can protrude into the dielectric layer 22, and the dielectric layer 22 can be sufficiently thin to allow the particles 16 to be in electrical communication with corresponding ones of the array of flat electrodes 20. For example, a polymeric dielectric layer 22 can have a thickness of about equivalent to or less than the grain size dimension of the printed particles. In preferred embodiments, the thickness of the dielectric layer 22 is less than the grain size dimension of the printed particles, specifically less than about 0.75 times the grain size dimension of the printed particles, or more specifically less than half the grain size dimension of the printed particles. Consequently, the protruding parts of the particles 16 can act as electrodes.

The conductive particles described above can be functionalized with inorganic salts or ions such as calcium, chloride, inorganic phosphorous, potassium, selenium, and sodium; proteins such as poly-L-lysine, laminin, bilirubin, albumin, insuline, hemoglobin, collagen, fibronectin, and fibrinogen; enzymes such as alkaline phosphatase, lactate dehydrogenase, and glutamate oxalacetate transaminase; carbohydrates such as glucose; lipids such as triglycerides nucleic acids, e.g., DNA, RNA, m-RNA, t-RNA, or selected portions thereof; vitamins such as beta-carotene, bioflavonoids, biotin, choline, CoQ-10, essential fatty acids, folic acid, hesperidin, inositol, para-aminobenzoic acid, rutin, vitamin A, vitamin B complex, vitamin B-1 thiamine, vitamin B-2 riboflavin, vitamin B-3 niacin/niacinamide, vitamin B-5 pantothenic acid, vitamin B-6 pyridoxine, vitamin B-9 folic acid, vitamin B-12 cyanocobalamine, vitamin B-15 dimethylglycine, vitamin B-17 leatrile or amygdalin, vitamin C, vitamin D, vitamin E, vitamin F unsaturated fats, vitamin G, vitamin J, vitamin K, and vitamin P; antibodies such as immunoglobulin A, immunoglobulin D, immunoglobulin E, immunoglobulin G, and immunoglobulin M; steroids and hormones such as cholesterol, cortisol, follicle stimulating hormone, growth hormone, leutinizing hormone, platelet-derived growth factor, fibroblast growth factor, parathyroid hormone, progesterone, prolactin, prostaglandins, testosterone, and thyroid stimulating hormone; aminoacids such as alanine, arginine, asparagine, aspartic acid, cysteine, glutamine, glutamic acid, glycine, histidine, isoleucine, leucine, lysine, methionine, phenylalanine, proline, serine, threonine, tryptophan, and valine; and aminoacid derivatives such as creatine.

In one embodiment, chemical functionalization of the particles is achieved by pre-treating the surface of the particles with a solution of a chemical moiety (e.g., proteins such as poly-L-lysine and laminin) in water for a duration of, for example, 2 hours. In another embodiment, the particles are treated after they have been printed into the dielectric layer 22.

As used herein, the terms "a" and "an" do not denote a limitation of quantity but rather denote the presence of at least one of the referenced items. Moreover, ranges directed to the same component or property are inclusive of the endpoints given for those ranges (e.g., "about 5 wt % to about 20 wt %," is inclusive of the endpoints and all intermediate values of the range of about 5 wt % to about 20 wt %). Reference throughout the specification to "one embodiment", "another embodiment", "an embodiment", and so forth means that a particular element (e.g., feature, structure, and/or characteristic) described in connection with the embodiment is included in at least one embodiment described herein, and might or might not be present in other embodiments. In addition, it is to be understood that the described elements may be combined in any suitable manner in the various embodiments. Unless defined otherwise, technical and scientific terms used herein have the same meaning as is commonly understood by one of skill in the art to which this invention belongs.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method of fabricating a semiconductor device, comprising:
    contacting a face of a printing plate with a liquid suspension comprising conductive particles to arrange the particles at predefined positions on the face of the printing plate, by moving the liquid suspension over the printing plate so as to embed a particle in each of a plurality of recessed features of the printing plate, and thereafter removing the liquid suspension such that the conductive particles remain only within the recessed features of the printing plate and protrude therefrom; and
    contacting a dielectric layer residing upon an array of electrodes disposed upon a semiconductor substrate with the face of the printing plate to transfer the conductive particles to a position in or on the dielectric layer.

2. The method of claim 1, wherein the conductive particles have a grain size dimension of less than or equal to about 100 micrometers.

3. The method of claim 1, wherein the conductive particles have a grain size dimension of less than or equal to about 100 nanometers.

4. The method of claim 1, wherein the conductive particles are aligned to the array of electrodes during said contacting of the dielectric layer with the face of the printing plate.

5. The method of claim 1, wherein the conductive particles comprise Cu, Au, Ag, Pt, Ir, W, Ta, Pd, Al, Ni, Co, a conductive oxide, or a combination comprising at least one of the foregoing.

6. The method of claim 1, wherein the conductive particles are substantially cube shaped or spherical shaped.

7. The method of claim 1, wherein the dielectric layer comprises a polymer.

8. The method of claim 1, wherein the dielectric layer is planarized prior to being contacted with the face of the printing plate.

9. The method of claim 1, wherein the conductive particles are functionalized with an inorganic ion, a protein, an enzyme, a nucleic acid, a vitamin, an antibody, a steroid, a hormone, an aminoacid, or a combination comprising at least one of the foregoing.

10. The method of claim 1, wherein each electrode in the array of electrodes has a lateral dimension of less than or equal to about 1000 micrometers.

* * * * *